United States Patent [19]

Andrieu et al.

[11] Patent Number: 5,552,269

[45] Date of Patent: Sep. 3, 1996

[54] MEANS FOR THE QUANTITATIVE DETERMINATION OF RETROVIRUS, METHOD FOR ITS PREPARATION, AND DIAGNOSTIC KIT CONTAINING SAID MEANS

[75] Inventors: Jean-Marie Andrieu; Wei Lu, both of Paris, France

[73] Assignee: Aremas (Association pour la Recherche, l'Etude, le Traitement et la Prevention des Maladies Malignes du Sang), France

[21] Appl. No.: 193,205

[22] PCT Filed: May 11, 1993

[86] PCT No.: PCT/FR93/00455

§ 371 Date: Jan. 12, 1994

§ 102(e) Date: Jan. 12, 1994

[87] PCT Pub. No.: WO93/23565

PCT Pub. Date: Nov. 25, 1993

[51] Int. Cl.$^6$ .............................. C12Q 1/70; C12Q 1/68; C12P 19/34

[52] U.S. Cl. .................. 435/5; 435/6; 435/91.2; 435/91.51

[58] Field of Search .......................... 435/6, 91.2, 91.51, 435/5

[56] References Cited

FOREIGN PATENT DOCUMENTS 9102817  8/1990  WIPO .

OTHER PUBLICATIONS

Kawasaki, Amplifications—A Forum for PCR Users, Sep. 1989, pp. 4–6.

Eron et al., 1992, Proc. Natl. Acad. Sci. U.S.A. 89:3241–3245.

Lu and Andrieu, 1992, J. Virology 66:334–340.

Bourinbaiar, 1991, Nature 349:111.

Genesca et al., 1990, J. Infectious Diseases 162:1025–1030.

*Primary Examiner*—George C. Elliott
*Attorney, Agent, or Firm*—Brumbaugh, Graves, Donohue & Raymond

[57] ABSTRACT

The invention relates to the diagnosis of retrovirus diseases.

In the quantitative determination of retrovirus in vitro, comprising means for the retrotranscription in viral DNA of viral RNA of samples of liquid and means for amplification of the viral DNA by polymerase chain reaction, a means for the quantification of the results is used which is composed of an external standard formed by samples of cell cultures infected by determined quantities of said retrovirus titrated in their reference viral protein (or "core protein"), said samples being distributed in liquid which is free of said virus, determined in parallel with the serum to be tested.

9 Claims, 4 Drawing Sheets

MEANS FOR THE QUANTITATIVE DETERMINATION OF RETROVIRUS, METHOD FOR ITS PREPARATION, AND DIAGNOSTIC KIT CONTAINING SAID MEANS

The present invention relates to the diagnosis in man and animals of diseases due to retrovirus and, in particular, the diagnosis of infection by the human immunodeficiency virus (HIV).

Retroviruses are part of the Retroviridae family and are RNA viruses which, due to their reverse or inverse transcription (hereinafter abbreviated "RT"), can transcribe their RNA genome into DNA. A retrovirus is thus able to be introduced into the cells which act as its host, in the form of chromosomal or extrachromosomal DNA. As a result, a retrovirus exists in two forms:

In free form, as mobile RNA genetic element, capable of passing from one cell to another;

In cell form retrotranscribed in DNA, which constitutes the form necessary for its multiplication.

In accordance with the present classification, the Retroviridae family is divided into three subfamilies: Onconvirinae, Spumavirinae and Lentivirinae.

For greater clarity, explanations which follow and the practical details of the invention which will be set forth further below are given with reference to the HIV retrovirus, which is part of the Lentivirinae family.

However, what is stated or shown with regard to this virus applies, *mutatis mutandis*, to other retroviruses. It is therefore understood that the present patent application is not limited to the human immunodeficiency retrovirus and that it is simply in a desire to simplify the description and/or the methodological indications that reference is primarily had thereto.

The importance of the diagnosis of infections by retrovirus and the problems relating thereto are summarized below:

Almost all persons who are seropositive for the human immunodeficiency virus (HIV) develop AIDS within a period of 3 to 15 years after infection.

The development of AIDS has, up to now, been fatal in all cases.

The present goals of the person skilled in the art is concerned with the developing of remedies or vaccines, methods of treatment, and/or methods of diagnosis are:

the evaluation of the prognosis of each seropositive patient, namely the determination of whether what one is confronted with in this patient is a rapid development towards AIDS or, on the contrary, of a lengthy stability of the infection; and the evaluation within a short time of the effectiveness of a drug in a seropositive patient. Up to the present time, this evaluation has required a very large number of patients and a long period of surveillance, due to the fact that the evaluation criteria adopted for a treatment are the triggering of AIDS or death, which events occur after years of development in a seropositive patient.

Research work during the last few years has led, in order to satisfy these two goals, to trying to evaluate the amount of virus itself present in the organism, either in the form of retrotranscribed virus in the form of DNA in the circulating cells of the blood and particularly in the T4 cells, or in the form of free virus in the serum of the patients (in the form of RNA).

At present, two techniques are known for measuring viral concentration.

A coculture technique makes it possible to measure, in vitro, the percentage of infected cells in the blood. This percentage is low (less than 1/30,000) in seropositive persons who will remain stable and asymptomatic for the following two or three years, but, on the other hand, high (greater than 1/3,000) in seropositive persons who are going to evolve rapidly towards AIDS. The study of these percentages also makes it possible to follow up the effectiveness of a drug.

However, this culture technique has drawbacks. In particular, it requires a laboratory qualified for active viral cultures, known as the P3 type. Furthermore, the operations corresponding to the culture can last up to 30 days, which is obviously too long for an important laboratory examination, which could possibly be used as routine in numerous patients.

A second type of technique is measurement of the viral DNA of the cells. The measurement of this DNA is effected by a process of physical-chemical amplification employing the well-known technique today of the polymerase chain reaction (commonly known by the abbreviation "PCR"). [See, for example, "Recent Advances in the Polymerase Chain Reaction" by H. A. Erlich, et al., Science 252:1643–1650, 1991]. In view of the poor reproducibility of the PCR from one experiment to another, the measurement must be carried out in the presence of a standard, which is introduced in each experiment in the form of plasmids in different concentrations, each containing a single copy of the viral DNA. In accordance with this technique (described, for instance, by J. W. Shih, et al. in the Journal of Infectious Diseases 162:1025–1030, 1990), by measuring simultaneously the viral DNA coming from these different concentrations of plasmids and the samples obtained from patients, one makes certain that the characteristics of the PCR are identical within one and the same operation. Thus, by means of a reference line obtained due to the plasmid viral DNA concentrations, the viral DNA present in the sample can be measured. The measurement of the vial DNA by the PCR makes it possible to establish the individual prognosis and to study the effectiveness of a drug used in a current treatment in the same manner as the percentage of cells infected. This technique requires expertise in PCR, but it does not require a qualified laboratory of P3 type, and about thirty samples can be treated in 2 or 3 days. Coculture as well as the measurement of the cellular DNA do not make it possible to measure the amount of virus produced in the organism, but only the amount of the retrotranscribed virus in the cells.

The measurement of the concentration of the virus in the serum is of major interest since, through it, there is a true reflection of the process of production of the virus by the cells and the process of destruction of the virus by different mechanisms, the concentration of the virus in the serum being then the resultant of these two processes.

There is therefore a need to effect the determination of this type of parameter and only measurement of the viral RNA permits this; in fact, the measurement of the infective power of the plasma is merely a very incomplete reflection of the concentration of the circulating virus, in view of the fact that, in almost all asymptomatic seropositive patients, serum antibodies neutralize the infectious activity of the virus.

It has now unexpectedly been found that this can be done by using a means for the quantitative determination of retrovirus in vitro comprising means for the retrotranscription in viral DNA of viral RNA of samples of liquids and means for amplification of the viral DNA by polymerase chain reaction (abbreviated "PCR") and comprising a means for quantifying the results which is formed of an external standard formed by samples of cultures of cells infected by given amounts of said retrovirus, which are standardized in their reference viral protein, said samples being distributed in standard liquid which is determined in parallel with the liquid to be tested.

The measurement of the RNA of the virus itself requires:

retrotranscription of the viral RNA in viral DNA, in practice due to the enzyme known as reverse or inverse transcriptase and the amplification of the DNA due to the above-mentioned PCR.

The second part of the operation is today well known and standardized as indicated above:

On the other hand, up to now, there has been no method which permits the standardization of the first part of the operation, that is to say, the passage of viral RNA into viral DNA. Now, the yield of the reverse transcriptase may vary from one operation to the other by a factor of as much as 2 log (namely a difference of 1 to 100).

The invention results in decisive progress in the means and methods of quantitative determination of retrovirus in vitro by providing a simple and effective means and technique for the standardizing of this passage of viral RNA into viral DNA.

As indicated above, this means comprises a means of quantification formed of a suitable external standard.

The first object of the invention is therefore a means for the quantitative determination of retrovirus in vitro, comprising means for the retrotranscription in viral DNA of viral RNA of samples of liquid and means for amplifying the viral DNA by polymerase chain reaction, characterized by the fact that it comprises a means for quantifying the results which is formed of an external standard formed by viral concentrations standardized in their reference viral protein, obtained from cultures of cells infected by the retrovirus concerned, said viral concentrations being distributed in a liquid free of said virus and identical to the liquid to be tested.

Another object of the invention is a method for the quantitative determination of retrovirus in vitro, comprising the retrotranscription in viral DNA of viral RNA of samples of liquid and the amplification of viral DNA by polymerase chain reaction, characterized by the fact that it comprises, for the quantification of the results, the use of an external standard formed by samples of cultures of cells infected by given quantities of said retrovirus which are standardized in their reference viral protein (or "core protein"), said samples being distributed in a liquid free of said virus, determined in parallel with the liquid to be tested.

Still another object of the present invention is a quantitative diagnostic kit comprising such a means, as well as the use thereof for the diagnosis of retrovirus diseases, particularly the HIV viruses, the other human and animal lentiviruses, human and animal oncoviruses and human and animal spumaviruses.

These objects, as well as others which will become evident from the following description, will be illustrated more specifically by reference to the examples and the accompanying figures to which it will be useful to refer, but which in no way limit the invention.

The reference proteins are, in particular, the core protein P24/25 for the HIV-1 viruses, the protein P27 for the HIV-2 viruses and the SIV viruses, and the protein P19 for the HTLV-1 viruses.

As to the virus serving to constitute the external standard according to the invention, it can, as a variant, be replaced by any other retrovirus having substantially the same characteristics as it in terms of viral RNA and protein.

By liquid, in the present invention, there is understood all biological liquids coming from the animal or vegetable world, such as, for example, serum, plasma, intracellular fluid, perspiration, urine, and also water of the rivers and others, but also laboratory liquids, such as the supernatants such as culture supernatants and others and, more generally, any other form of liquid, both natural and produced by man.

For the use of the means in accordance with the invention, it is advisable to have high concentrations of HIV obtained by culture of cells infected by HIV. This can be obtained by a method described by J.-M. Andrieu and W. Lu in Journal of Virology, January 1992, pages 334–340.

Since in the supernatants of viral cultures the protein concentration (in the present case P24 protein) which is not bound to the virus or is free is insignificant (less than 1%), the protein concentration is proportional to the number of viral proteins (Cf. A. S. Bourinbaiar, Nature 349, Jan. 10, 1991).

It is now proposed, in accordance with the present invention, to develop an external standard composed preferably of increasing concentration of viruses titrated in P24. For this, there are advantageously used quantities of viruses substantially equivalent to 100, 10, 1 and 0.1 pg of P24 distributed in about 0.5 ml of standard liquid which is subjected to the same operations as the liquid to be tested.

It has been able to note by this means that a concentration of RNA obtained by retrotranscription, then PCR (measured in counts per minute, abbreviated cpm) is perfectly proportional to the concentration of virus initially present (measured in P24).

It is therefore recommended henceforth, in accordance with the present invention, that the HIV, the concentration of which is measured by the study of the concentration of the P24 protein, be used as external standard for the determination of the RNA concentration of the virus present in the serum of the patients.

In order to make certain of the completely reproducible nature of this external standard in accordance with the invention, various types of operations were carried out. First of all, viruses coming from seropositive persons and persons having AIDS respectively who come from different geographic regions were compared and were found to give the same concentrations of viral RNA, provided that the same concentration of P24 proteins had been used.

In fact, it was also able to show that, whatever the individual geographical origin of the virus (HIV-1), similar concentration of core protein were associated with:

(1) on the one hand, a similar infective power of human lymphocytes (see J.-M Andrieu and W. Lu, op. cit.), (2) on the other hand, substantially identical concentrations of viral RNA.

Furthermore, it was observed that the RNA coming from heat-inactivated viruses (1 hour at about 56° C.) has exactly the same properties as the RNA coming from the infectious virus; the same virus concentrations measured in P24 proteins give rise to the same concentrations of viral RNA.

By way of specific example of the use of these means in accordance with the invention, we proceeded as follows:

A culture supernatant of infectious or heat-inactivated HIV-1, as the case may be, having a known number of viral particles (deduced by measurement of the content of P24 protein associated with the virion) was diluted serially in human AB serum (100, 100, 10 and 1 pg/ml). An aliquot portion of 500 μof each viral culture supernatant dilution or 500 μl of serum samples of patients were formed into pellets by centrifuging and extracted by the RNAzol®B method (Wak-Chemie Medical GmbH). The RNA samples were placed again in suspension in 50 μof water treated with diethyl pyrocarbonate, containing 1 mM of DTT (Sigma) and 5 U of RNAsin (Promega). After treatment with 2 U of DNase I free of RNase (Promega), two aliquot portions of 10 μof each RNA sample were subjected to retrotranscription and amplified for a specific gag gene of HIV-1 with an RNA PCR kit (Perkin Elmer Cetus) using SK 104/SK 145 primers. The specificity of the PCR was tested by simultaneous amplification of DNA of cloned HIV [BH-10 (HTLV-3-B)] and Southern-blot analysis (transfer of DNA) for each experiment. A PCR was carried out in parallel in the absence of reverse transcriptase and/or of copy model (template) as negative controls. Two aliquot portions of 10 μl of each of the amplified PCR products were directly transferred onto a nylon membrane and tested with an SK 19 labeled at its ends with gamma$^{32}$P. The signal of the PCR product was quantified by determining the radioactive value in cpm (counts per minute). The standard curve of RNA viral particles for each batch of experiments was determined on basis of the average and the standard deviation of an iteration of four points of each of the dilutions. The evaluations of the serum samples of the patients were effected by a formula derived from the standard curve. It was thus possible to verify that the standard lines obtained during the different operations always remained parallel to the control standard lines of the PCR of DNA and served as controls of the sensitivity and reproducibility of the PCR.

The results obtained in the experiments carried out in accordance with this description are shown in the accompanying FIGS. 1 to 8.

These figures are graphs in which the log of the number of counts per minutes (cpm) counted with a Geiger counter as quantification of the signal of the PCR product is plotted on the abscissa and the number of RNA/DNA copies is plotted on the ordinate.

The bottom reference line is the DNA standard (for different concentrations of viral plasmid). The reference line resulting from the external standard in accordance with the invention is in all cases substantially parallel to the DNA standard and in particular its deviation from the standard curve is variable from one operation to the next, which confirms beyond dispute the necessity of the standard in accordance with the present invention. This is related to a reverse transcriptase activity which is similar within the same operation but different from one operation to the next.

It is thus verified that, for the standard virus dilutions, the retrotranscription ratio is substantially constant within the same operation.

Other elements relative to the results of these comparative tests for which the means in accordance with the invention were used are set forth in Tables 1 and 2 below.

Thus, the present invention makes it possible to establish that an external standard coming from a pool of viruses or of equivalent viral strains, preferably inactivated by heat or any equivalent means, coming from a large number of patients infected by the retrovirus concerned, can be used by any laboratory which desires to measure the concentration of said virus.

In practice, it is recommended that four concentrations be used, preferably of inactivated virus, distributed in standard liquid which is subjected to all of the operations in the same way as the liquid tested, in order to obtain a reference line.

In practice, it is advisable to establish this standard upon each operation.

TABLE 1

Figure 1:
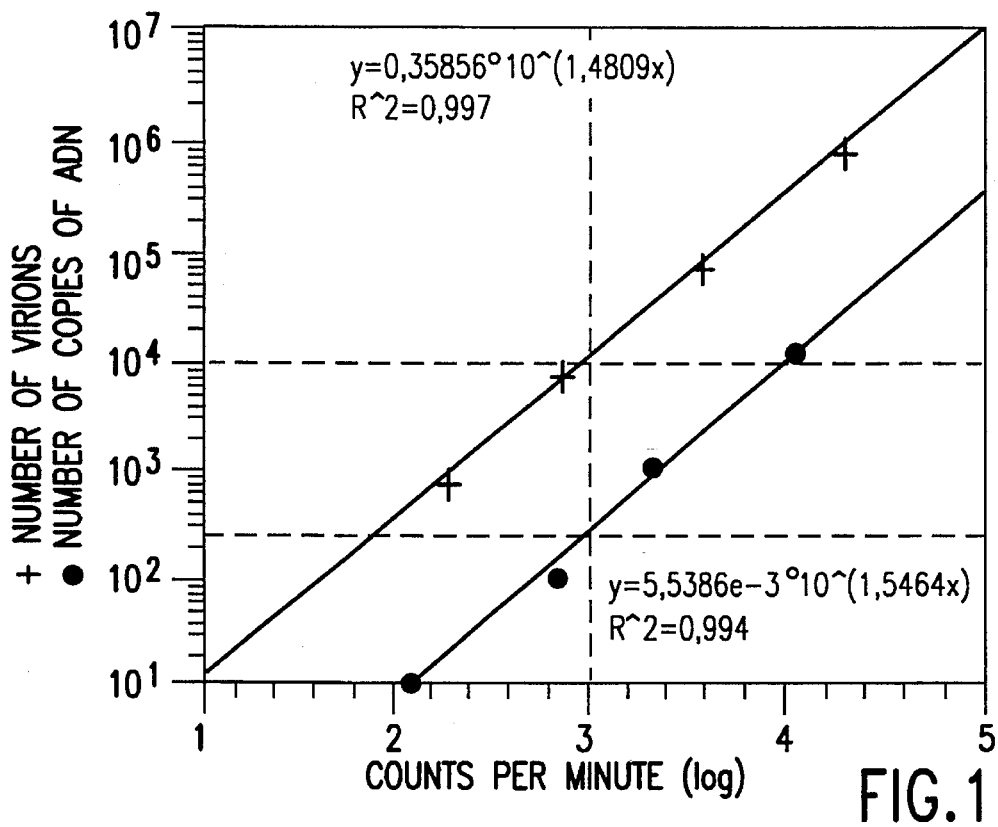
FIGS. 1–8. Representation of standard curves used in the quantiatation of retrovirus, with each set derived from an independent experiment. The bottom reference line is a DNA standard derived from RT-PCR of different concentrations of viral plasmid. The upper reference line is a standard curve derived from RT-PCR of known concentrations of virus particles which were standardizd in their viral reference protein. The figures are graphs in which the log of the number of counts per minute (cpm), as derived from a Southern blot, is used for quantification of the signal of the PCR product. Each graph shows a plot of the amounts of virions and copies of DNA, respectively, versus cpm.
Figure 2:
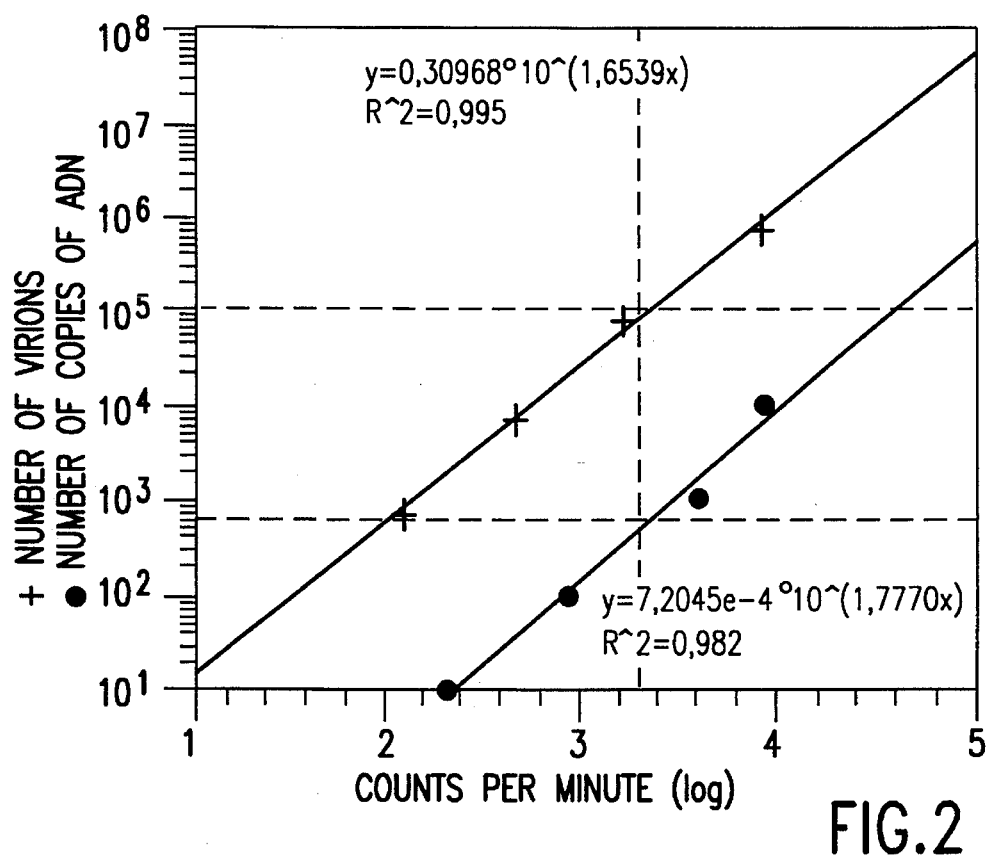
Figure 3:
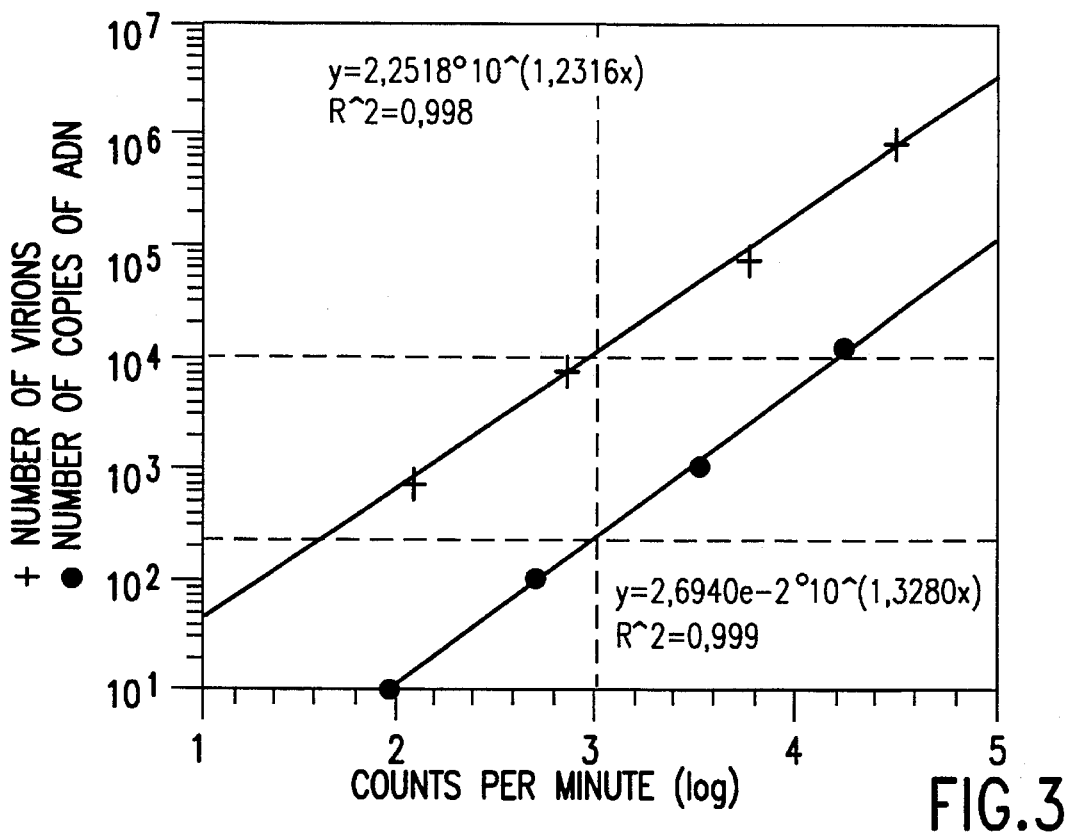
Figure 4:
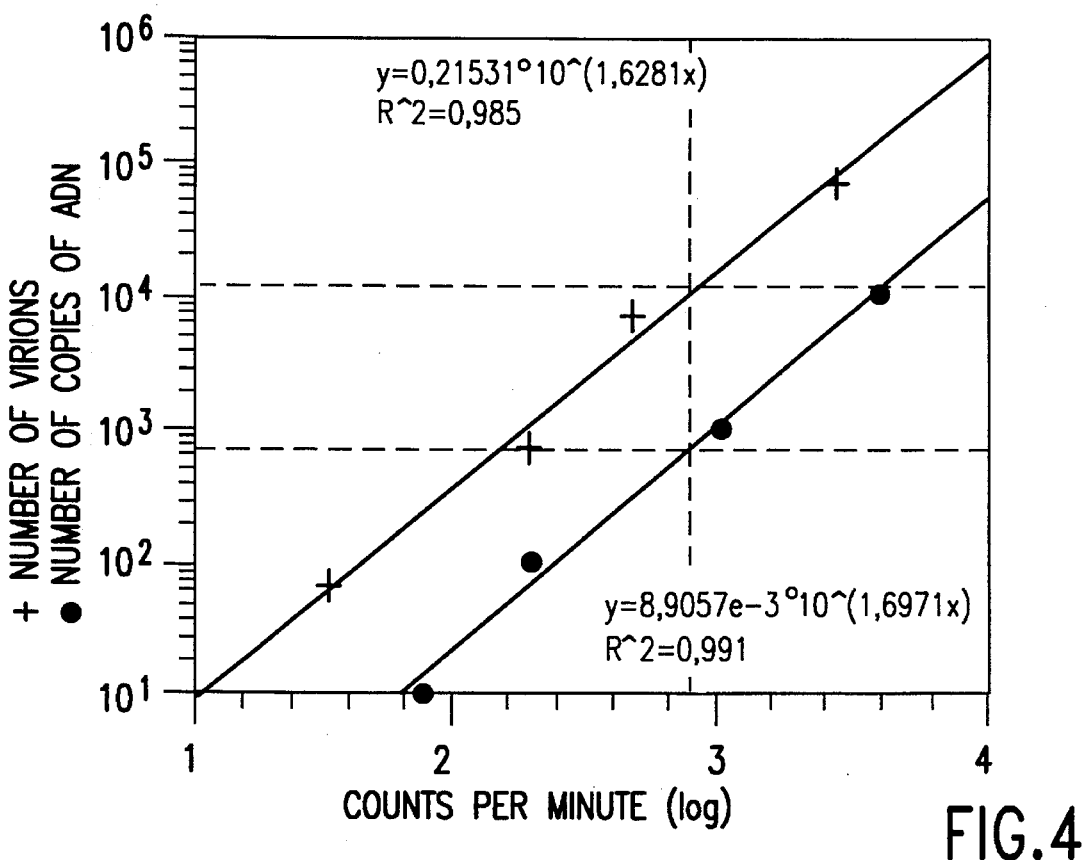
Figure 5:
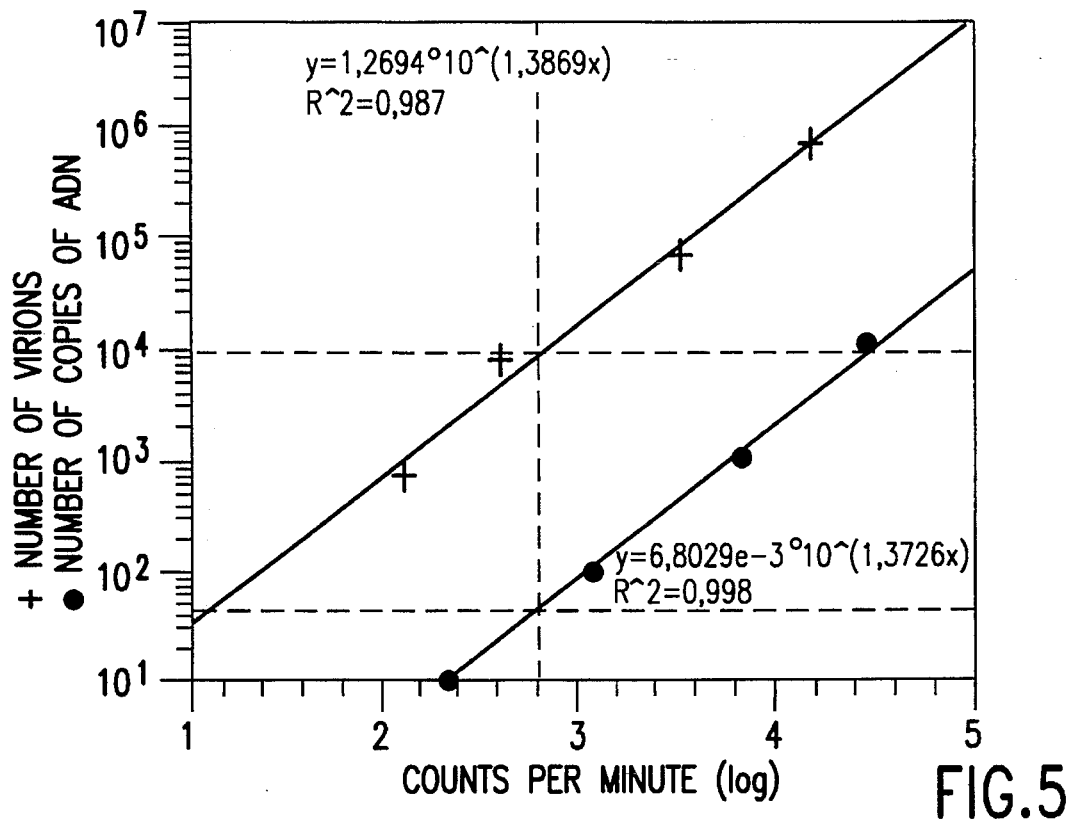
Figure 6:
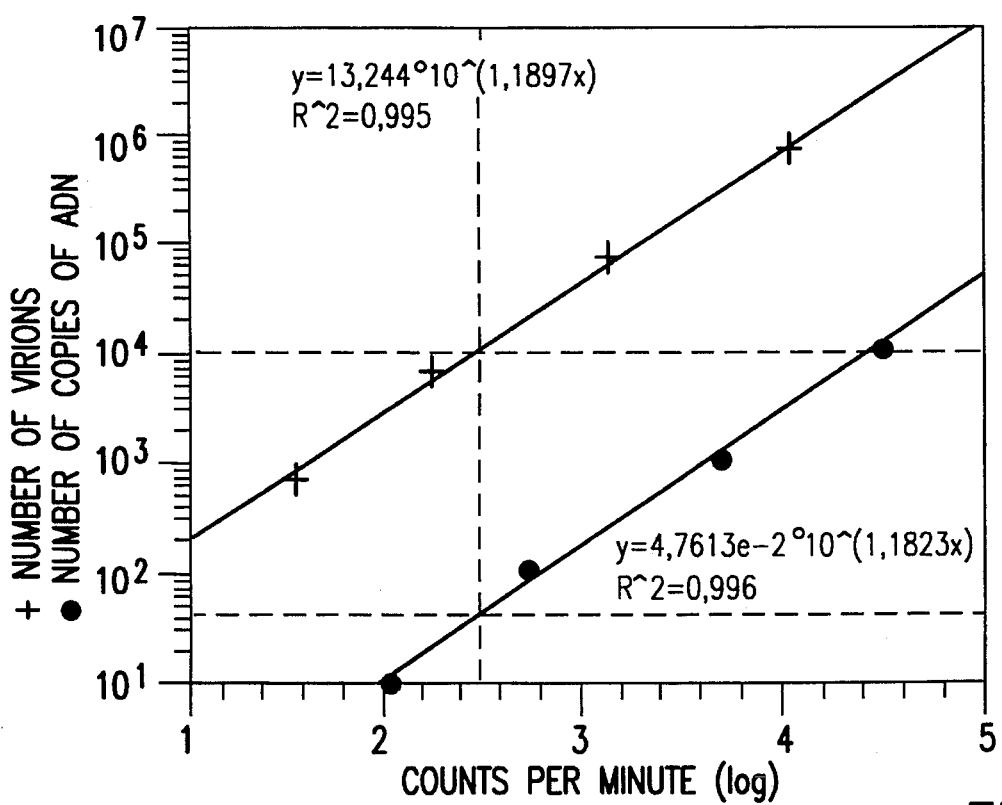
Figure 7:
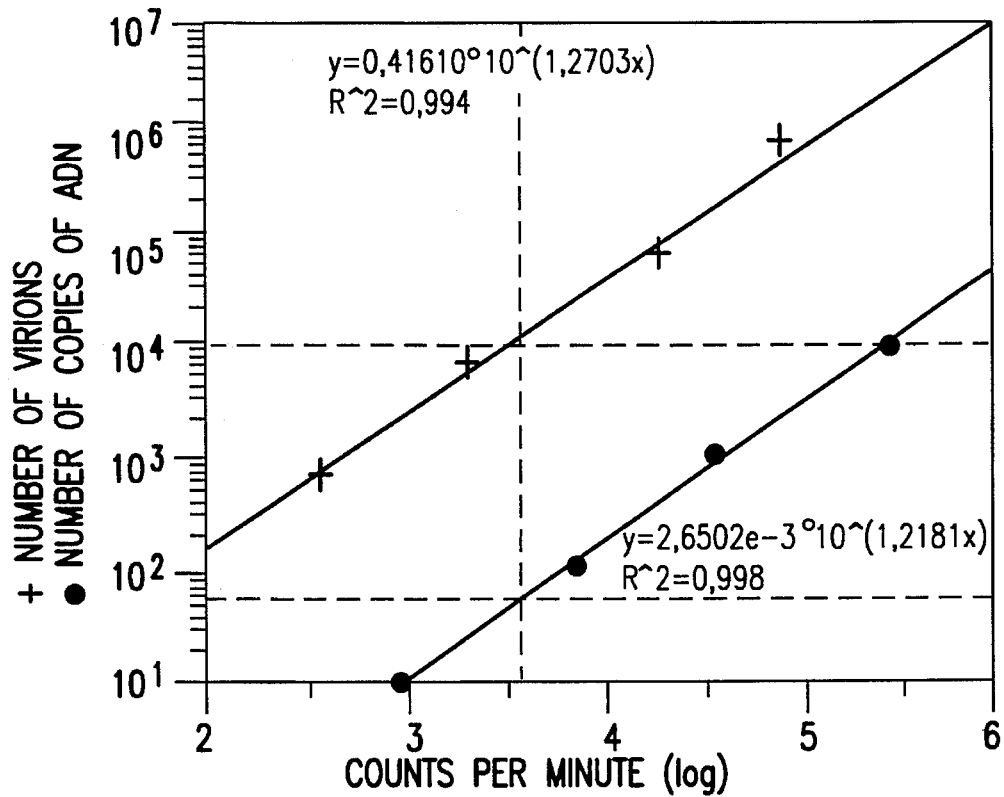
Figure 8:
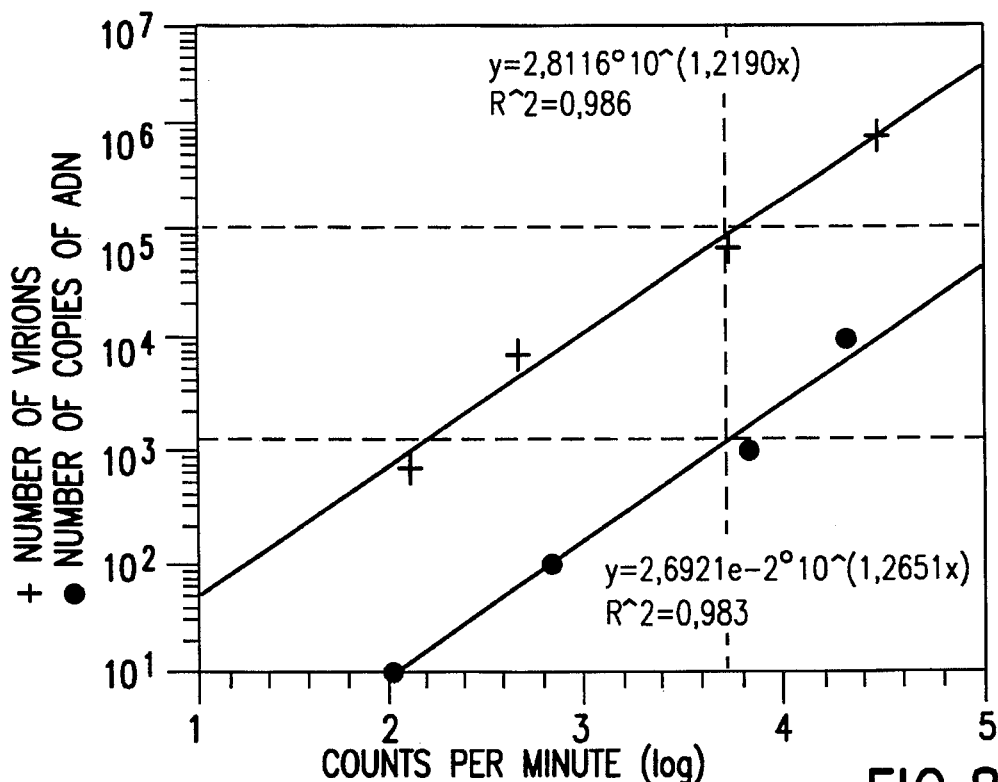

Quantification of the viral particles (vp) of HIV-1 of the serum of patients by RNA (TR)-PCR using the viral strain with a known number of vp of HIV-1 as external standard.

| Stage of the Patients according to CDC | Circulating CD4 T Cells/μl | Mean ± Standard Deviation | |
|---|---|---|---|
| | | of vp/intra-test variation | of vp/inter-test variation |
| | | (log max-log min) | |
| | | (1) | (2) |
| CDC II (asymptomatic) | 934 | 469 ± 85 /(0.282) | 481 ± 212 /(0.532) |
| CDC III (asymptomatic) | 674 | 4021 ± 624 /(0.253) | 3788 ± 1535 /(0.471) |
| CDC IVc (SK) | 380 | 377946 ± 71459 /(0.279) | 410673 ± 125556 /(0.538) |
| CDC IVb (IO) | 34 | 1559378 ± 265742 /(0.322) | 1368712 ± 436657 /(0.526) |

(1): The serum samples were tested five times in one experiment.
(2): The serum samples were tested on five different lots in the experiment.
In the above Table 1:
CDC = Centers of Disease Control (Atlanta, USA)
SK = Kaposi's sarcoma
IO = Opportunistic infection Table 1 shows the similarity of viruses coming from very different patients and the intra-test and inter-test variations.

TABLE 2

Amplification by RNA (TR)-PCR of 100 pg of infectious or
heat-inactivated HIV-1 strains isolated from
asymptomatic patients or patients having AIDS.

| | | Quantitative Measurement of Amplification by Reverse Transcriptase, then PCR | |
|---|---|---|---|
| Stage of the Patients according to CDC | Circulating CD4 T Cells/µl | Infectious HIV (Mean ± SD of cpm) | Inactivated HIV Mean ± SD of cpm) |
| CDC II (asymptomatic) | 934 | 15441 ± 2046 | 17646 ± 299 |
| CDC III (asymptomatic) | 674 | 15110 ± 2170 | 15511 ± 2108 |
| CDC IVc (SK) | 380 | 15756 ± 2867 | 10479 ± 1202 |
| CDC IVb (IO) | 34 | 17019 ± 2757 | 16988 ± 3007 |

*This corresponds to $10^6$ viral particles
**The serum samples were tested five times in one experiment

We claim:
1. A method for the quantitative determination of retroviruses in vitro, comprising (1) performing reverse transcription of an RNA viral genome of a retrovirus in a test sample to produce a DNA copy; (2) performing polymerase chain reaction amplification of the DNA copy of the RNA viral genome to produce a plurality of DNA copies; (3) performing quantitative hybridization of the DNA copies to a plurality of complementary DNA probes to measure the DNA content of the test sample; and (4) converting the DNA content from the test sample to a viral particle number by reference to a standard curve of DNA content derived from reverse transcription-polymerase chain reaction of a plurality of concentrations of retrovirus standardized in their concentration of a viral reference protein.

2. The method of claim 1, in which the retrovirus is selected from the group consisting of HIV-1, HIV-2, HTLV-1, HTLV-2 and SIV.

3. The method according to claim 1, in which the viral reference protein is selected from the group consisting of a p24 protein, a p24/p25 core protein, a p27 protein, and a p19 protein.

4. The method according to claim 1, in which the test sample is an animal or human serum.

5. The method according to claim 1, in which the virus concentrations standardized in their reference protein are standardized to 100, 10, 1 and 0.1 pg of viral reference protein.

6. A diagnostic kit for the quantitative determination of retroviruses in vitro, using the method of claim 1.

7. A method for the diagnosis of retrovirus disease, using the method of claim 1.

8. The method of claim 7, in which the retrovirus is selected from the group consisting of HIV, lentiviruses, spumaviruses and oncoviruses virus groups.

9. The method of claim 8, in which the retrovirus is derived from an animal or a human.

* * * * *

UNITED STATES PATENT AND TRADEMARK OFFICE
CERTIFICATE OF CORRECTION

PATENT NO. : 5,552,269

DATED : Sept. 3, 1996

INVENTOR(S) : Andrieu and Lu

It is certified that error appears in the above-indentified patent and that said Letters Patent is hereby corrected as shown below:

Col. 2, line 38, "vial" should read --viral--;

Col. 4, line 64, "$\mu$of" should read --$\mu$l of--;

Col. 5, line 1, "$\mu$of" should read --$\mu$l of--;

Col. 5, line 5, "$\mu$of" should read --$\mu$l of--;

Col. 6, line 26, "quantiatation" should read --quantitation--;

Col. 8, lines 37-38, "lenti-viruses, spumaviruses and oncoviruses" should read --lentivirus, spumavirus and oncovirus--.

Signed and Sealed this

Twenty-eighth Day of January, 1997

Attest:

BRUCE LEHMAN

Attesting Officer    Commissioner of Patents and Trademarks